US00PP29117P2

(12) United States Plant Patent
Podaras

(10) Patent No.: US PP29,117 P2
(45) Date of Patent: Mar. 13, 2018

(54) ***MIMULUS* PLANT NAMED 'PPOMIM2'**

(50) Latin Name: ***Mimulus naiandinus*×*Mimulus cupreus***
Varietal Denomination: PPOMIM2

(71) Applicant: Peter Podaras, Salem, OR (US)

(72) Inventor: Peter Podaras, Salem, OR (US)

( * ) Notice: Subject to any disclaimer, the term of this patent is extended or adjusted under 35 U.S.C. 154(b) by 0 days.

(21) Appl. No.: 15/330,273

(22) Filed: Sep. 1, 2016

(51) Int. Cl.
*A01H 5/02* (2006.01)

(52) U.S. Cl.
USPC ..... Plt./454

(58) Field of Classification Search
USPC ..... Plt./454
See application file for complete search history.

*Primary Examiner* — Anne M Grunberg
(74) *Attorney, Agent, or Firm* — Penny J. Aguirre

(57) ABSTRACT

A new cultivar of interspecific *Mimulus* plant named 'PPOMIM2' that is characterized by its floriferous blooming habit, its flowers that are large in size, its strong plant vigor and its flowers that are deep rose red in color.

2 Drawing Sheets

Botanical classification: *Mimulus naiandinus*×*Mimulus cupreus.*

Cultivar designation: 'PPOMIM2'.

BACKGROUND OF THE INVENTION

The present invention relates to a new and distinct cultivar of *Mimulus* of interspecific origin. The new cultivar will be referred to hereafter by its cultivar name, 'PPOMIM2'. 'PPOMIM2' represents a new cultivar of monkey flower grown for landscape and container use.

The new cultivar of *Mimulus* is a selection from a controlled breeding program conducted by the Inventor in Silverton, Oreg.

'PPOMIM2' was derived from a cross-made in 2014 under controlled conditions between *Mimulus naiandinus* 'Mega' (not patented) as the female parent a plants from the seed strain *Mimulus cupreus* 'Red Emperor' (not patented) as the male parent. 'PPOMIM2' was selected in 2015 as a single unique plant amongst the resulting seedlings.

Asexual propagation of the new cultivar was first accomplished by stem cuttings under the direction of the Inventor in Silverton, Oreg. in 2015. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'PPOMIM2' as a unique cultivar of *Mimulus.*

1. 'PPOMIM2' exhibits a floriferous blooming habit.
2. 'PPOMIM2' exhibits flowers that are large in size.
3. 'PPOMIM2' exhibits strong plant vigor.
4. 'PPOMIM2' exhibits flowers that are deep rose red in color.

The female parent of 'PPOMIM2' differs from 'PPOMIM2' in having flowers that are smaller in size and light pink-purple and white bi-colored and in having a less vigorous growth habit. The male parent of 'PPOMIM2' differs from 'PPOMIM2' in having flowers that are smaller in size, flowers that are deep red in color and a less vigorous growth habit. 'PPOMIM2' can also be compared to the cultivar *Mimulus cuperous* 'Highland Red' (not patented). 'Highland Red' differs from 'PPOMIM2' in having flowers that are more red in color.

BRIEF DESCRIPTION OF THE DRAWINGS

The accompanying photographs illustrate the characteristics of a 6 month-old plant as grown in a greenhouse in a one-gallon container in Mount Vernon, Wash.

The photograph in FIG. 1 provides a side view of 'PPOMIM2' in bloom.

Figure 1:
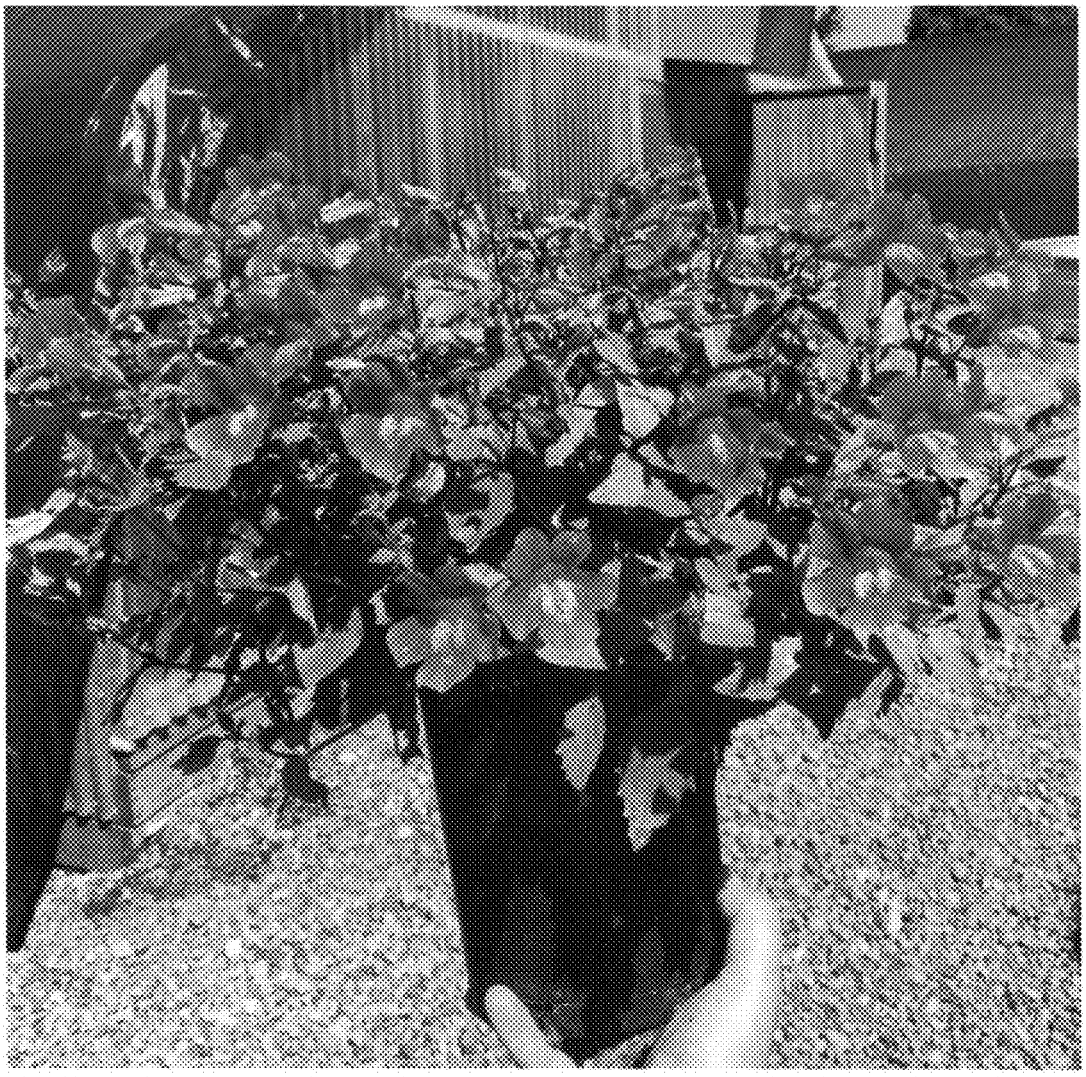
Figure 2:
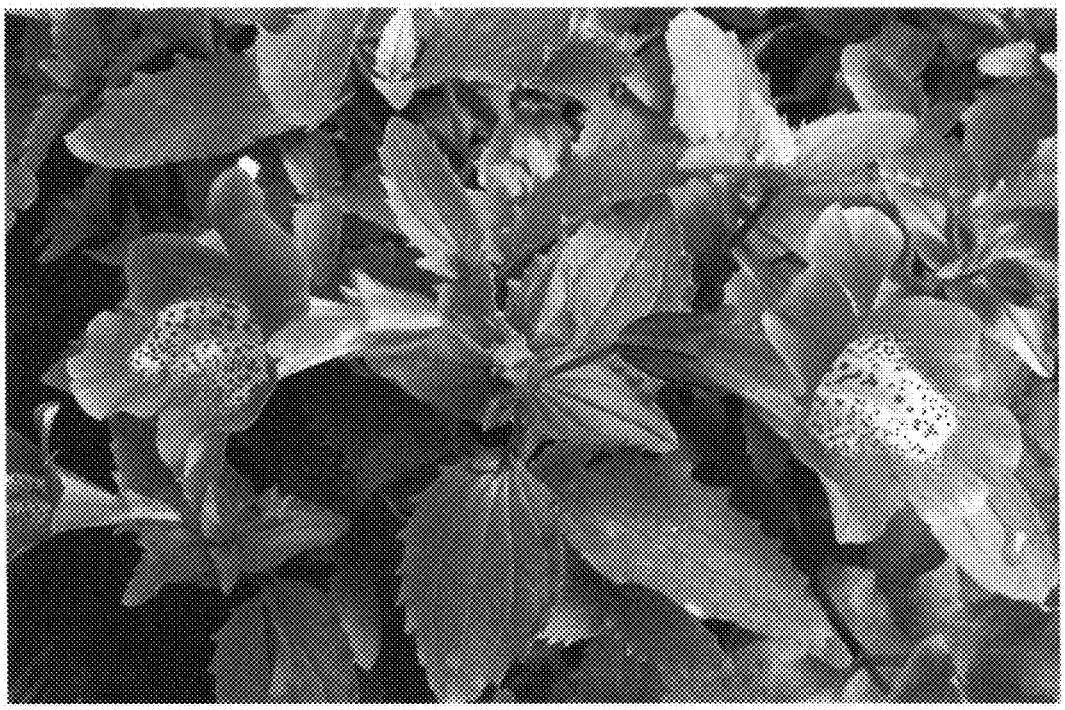

The photograph in FIG. 2 provides a close-up view of the flowers of 'PPOMIM2'.

The colors in the photograph may differ slightly from the color values cited in the detailed botanical description, which accurately describe the colors of the new *Mimulus.*

DETAILED BOTANICAL DESCRIPTION

The following is a detailed description of six month-old plants of the new *Mimulus* as grown outdoors in two-gallon containers in Mount Vernon, Wash. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Blooming period.*—From spring until first frost in Oregon.

*Plant type.*—Herbaceous annual.

*Plant habit.*—Trailing groundcover.

*Height and spread.*—An average of 38 cm in height and 42 cm in spread.

*Hardiness*.—At least to U.S.D.A. Zone 9, grown as an annual.

*Diseases and pests*.—No resistance and susceptibility to diseases or pests has been observed.

*Propagation*.—Softwood stem cuttings.

*Growth rate*.—Vigorous.

*Root description*.—Fibrous and fine, 155B in color.

*Time required for root initiation*.—An average of 5 days for root initiation with a young rooted plant produced after 2 to 3 weeks.

Stem description:

*Type*.—Basal.

*Shape*.—Rounded.

*Stem color*.—144B suffused with a blend between 181A and 186A.

*Stem size*.—An average of 20 cm in length and 4 mm in width.

*Stem surface*.—Glabrous and satiny.

*Internode length*.—An average of 3 cm.

*Branching*.—Freely branched with numerous basal stems creeping along the ground.

Foliage description:

*Leaf division*.—Simple.

*Leaf arrangement*.—Opposite.

*Leaf attachment*.—Clasping and sessile.

*Leaf size*.—An average of 35 cm in length and 2 cm in width.

*Leaf shape*.—Oval.

*Leaf base*.—Cuneate.

*Leaf apex*.—Acute.

*Leaf venation*.—Multi-nerved, color on the upper surface; inconspicuous, matches the color of the leaf surface, color on the lower surface; the color of the leaf surface towards the apex fading to 187A towards the base.

*Leaf number*.—An average of 8 pairs of leaves per stem 20 cm in length.

*Leaf margins*.—Serrate.

*Leaf aspect*.—Horizontal to slightly recurved.

*Leaf surface*.—Glabrous, smooth, and satiny on upper and lower surfaces.

*Leaf color*.—Young and mature leaves upper surface; 143A, young and mature leaves lower surface; 138B.

Inflorescence description:

*Inflorescence type*.—Single axillary flowers, solitary or in groups of two, blooms on current year's growth.

*Inflorescence size*.—An average of 4 cm in depth and 3 cm in width.

*Flower type*.—Zygomorphic salverform with bilabiate apex.

*Flower aspect*.—Upwards and outwards, held above foliage.

*Flower size*.—An average of 3.5 cm in length and diameter at apex and 8 mm in diameter at base.

*Lastingness of flowers*.—Individual flowers last about 5 to 7 days, self-cleaning.

*Flower quantity*.—An average of 8 solitary flowers per plant are open at any one time.

*Flower buds*.—Elongated elliptic shape with 5 longitudinal ribs, an average of 2 cm in length and 5 mm in width, color; 143B suffused with 186A.

*Flower fragrance*.—None.

*Peduncles*.—Rounded in shape, an average of 1 cm in length and 1 mm in diameter, 144A heavily suffused with 187B in color, puberulent surface, strong.

*Calyx*.—Campanulate, an average of 7 mm in diameter and 1.5 cm in length, 144B to 144C lightly suffused with 187B in color, persistent, color fades to a blend between 195B and 199B.

*Sepals*.—5, fused base; an average of 1.2 cm in length and 8 mm in width, free tips; triangular in shape, acute apex, entire margin, an average of 2.5 mm in length and 5 mm in width, color; 144B to 144C lightly suffused with 187B, glabrous and satiny on both surfaces.

*Corolla*.—Zygomorphic and bilabiate with base fused into a tube, reflexed upper lip; an average of 2.1 cm in width and 1.2 cm in length, lower lip; an average of 3.3 cm in width and 1.2 in length, tube; an average of 2.5 cm in length and 7 mm in width color; a blend between 61B and 10B to 10C.

*Petals*.—5, with 3 forming the lower lip and 2 forming the reflexed upper lip, base fused into an elongated tube, apices free and round in shape with entire, slightly undulate margin, an average of 1.2 cm in length and width, apex of central lobe on lower lip is retuse, upper and lower surfaces are smooth and satiny, color; upper lip inner surface; 61B, lower lip inner surface; 61B with 10B to 10C spotted by 61B at the base of the central lobe, upper lip outer surface; 64B, lower lip outer surface; 72B fading to 186D at the tip, tube inner surface; 72C fading from upper lip, 72C heavily suffused with 10A spotted with 61B fading from lower lip, fading to 157C around the entire base, tube outer surface; 64D fading from upper lip, 10C suffused and spotted with 61D fading from lower lip, fading to 150D around the entire base.

Reproductive organs:

*Gynoecium*.—Pistil; 1, an average of 2.4 cm in length, stigma; fan-shaped, an average of 3 mm in length and width, and 150C in color, style; an average of 1.5 cm in length and 0.7 mm in width, 157B to 157D in color, ovary; superior, elongated oval in shape, an average of 6 mm in length and 2.1 mm width, 149B in color.

*Androcoecium*.—Stamens; 4, anthers; dorsifixed, bifid, an average of 1.2 mm in length and width, 10C in color, filaments; an average of 2 cm in length and 0.7 mm in width, adnate to corolla at the base, NN155C in color, pollen; moderate in quantity and 10B to 10C in color.

*Seed*.—None observed to date.

It is claimed:

1. A new and distinct cultivar of *Mimulus* plant named 'PPOMIM2' as herein illustrated and described.

* * * * *